(12) United States Patent
Peterfeso et al.

(10) Patent No.: US 6,298,272 B1
(45) Date of Patent: *Oct. 2, 2001

(54) HIGH IMPEDANCE ELECTRODE TIP WITH INTERNAL DRUG DELIVERY CAPABILITY

(75) Inventors: Randall M. Peterfeso, St. Paul; Jeffrey T. Bartig, Maplewood, both of MN (US)

(73) Assignee: Cardiac Pacemakers, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/280,610

(22) Filed: Mar. 29, 1999

(51) Int. Cl.$^7$ ........................................... A61N 1/05
(52) U.S. Cl. .................................................. 607/120
(58) Field of Search ................................. 607/127, 121, 607/120

(56) References Cited

U.S. PATENT DOCUMENTS

| | | | |
|---|---|---|---|
| 4,819,661 | 4/1989 | Heil, Jr. et al. | 128/786 |
| 5,003,992 * | 4/1991 | Holleman et al. | 607/120 |

(List continued on next page.)

FOREIGN PATENT DOCUMENTS

| | | | |
|---|---|---|---|
| 0422363 | 8/1990 | (EP) | A61N/1/05 |
| WO 92/20401 | 4/1991 | (WO) | A61N/1/39 |
| WO 99/30772 | 6/1999 | (WO) | A61N/1/05 |

*Primary Examiner*—Scott M. Getzow
(74) *Attorney, Agent, or Firm*—Schwegman, Lundberg, Woessner & Kluth, P.A.

(57) ABSTRACT

An implantable lead, being either a fixed or retractable/extendable lead, having a distal tip electrode is adapted for implantation on or about the heart and for connection to a system for monitoring or stimulating cardiac activity. The electrode includes a mechanical fastener such as a fixation helix for securing the electrode to cardiac tissue, which may or may not be electrically active. The implantable electrode with a helical tip may comprise:

an electrode having a distal end and a proximal end; and
  a helix disposed within the electrode, which helix is aligned along a radial axis of the electrode to the distal end; and
  the implantable electrode having at least one feature selected from the group consisting of:
   a) the helix having a coating of an insulating material on its surface,
   b) the helix having its surface beyond the distal end of the electrode and the distal end of the electrode having a porous conductive surface at a base of the helix,
   c) a porous conductive element, screen or mesh at a base of the helix, and
   d) a porous conductive element at the end of the electrode having an insulating coating covering from 5–95% of the surface of the porous conductive element.

The electrode may further include an electrode tip having a porous electrical conductive element, such as a mesh screen, disposed on a surface at the distal end of the electrode tip, which can be used as a sensing or pacing interface with the cardiac tissue. The porous electrically conductive element will usually be positioned at the base of the helix (when extended if extendable/retractable). The mesh or screen may provide a guiding mechanism for the helix as it travels out of the electrode for securing the electrode to the heart or other muscle or organ. The guiding mechanism may include a groove within the mesh screen. Alternatively, the guiding mechanism includes a guiding bar on which the fixation helix rides on during extension or retraction. In combination with each of these high impedance tips, a drug delivery system is provided at least the majority of which drug delivery system is provided from a source within a volume which is within the structural walls of the lead and/or within a volume having its major dimensions and/or at least 50% of its volume generally within the projected area of the tip.

31 Claims, 6 Drawing Sheets

U.S. PATENT DOCUMENTS

| | | | |
|---|---|---|---|
| 5,217,028 | 6/1993 | Dutcher, et al. | 128/785 |
| 5,300,108 | 4/1994 | Rebell et al. | 607/127 |
| 5,522,874 * | 6/1996 | Gates | 607/120 |
| 5,776,178 * | 7/1998 | Pohndorf et al. | 607/120 |

* cited by examiner

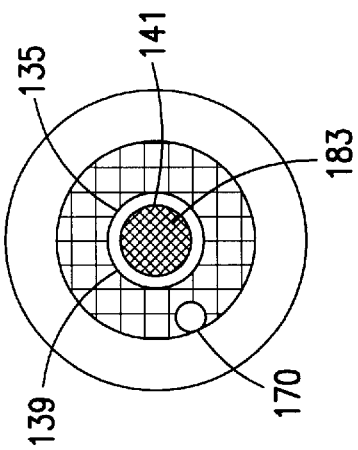
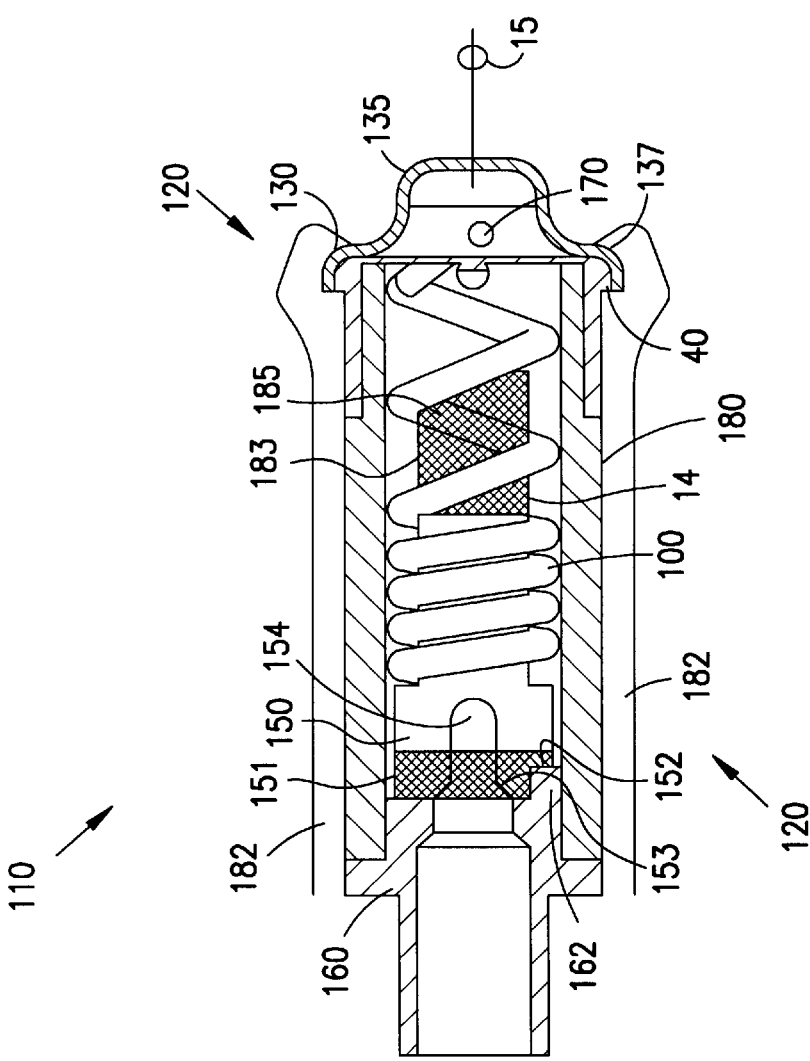

HIGH IMPEDANCE ELECTRODE TIP WITH INTERNAL DRUG DELIVERY CAPABILITY

BACKGROUND OF THE ART

1. Field of the Invention

The present invention relates generally to leads for conducting electrical signals to and from the heart. More particularly, it pertains to electrode tips for delivering electrical charges to the heart, and to tips which tend to reduce power consumption from cells without reducing the effective level of each pacing pulse, and to such tips with drug delivery capability from an internal source on a lead or support element carrying the tip.

2. Background of the Invention

Leads implanted in the body for electrical cardioversion or pacing of the heart are generally known in the art. In particular, electrically transmissive leads may be implanted in or about the heart to reverse (i.e., defibrillate or cardiovert) certain life threatening arrhythmias or to stimulate contraction (pacing) of the heart. Electrical energy is applied to the heart via the leads to return the heart to normal rhythm. Leads have also been used to sense conditions, materials or events (generally referred to as "sense" or "sensing") in the body, such as in the atrium or ventricle of the heart and to deliver pacing pulses to the atrium or ventricle. Tachy leads generally can at least sense, pace, and deliver defibrillation shocks. Brady leads can at least perform the combination functions of pacing and sensing the heart. One of the available functions of the pacemaker or the automatic implantable cardioverter defibrillator (AICD) is to receive signals from a lead and interpret signals. In response to these signals, the pacemaker can decide to pace or not pace. The AICD can decide to pace or not pace, and shock or not shock. In response to a sensed bradycardia or tachycardia event, a pulse generator produces pacing or defibrillation pulses to correct the condition. The same lead used to sense the condition is sometimes also used in the process of delivering a corrective pulse or signal from the pulse generator of the pacemaker.

Sick sinus syndrome and symptomatic AV (atrial-ventricular) block constitute two of the major reasons for insertion of cardiac pacemakers today. Cardiac pacing may be performed by the transvenous method or by leads implanted directly onto the ventricular epicardium. Most commonly, permanent transvenous pacing is performed using a lead positioned within one or more chambers of the heart. A lead, sometimes referred to as a catheter, may be positioned in the right ventricle or in the right atrium through a subclavian vein or other vascular port, and lead terminal pins are attached to a pacemaker which is implanted subcutaneously. The lead may also be positioned in both chambers, depending on the lead, as when a lead passes through the atrium to the ventricle. Sense electrodes may be positioned within the atrium or the ventricle of the heart as appropriate for the particular condition or the choice of the medical practitioner.

Pacemaker leads represent the electrical link between the pulse generator and the heart tissue which is to be excited. These pacemaker leads include single or multiconductor coils of insulated wire having an insulating sheath. The coils provide a cylindrical envelope or tube, many times referred to as a lumen, which provides a space into which a stiffening stylet can be inserted. The conductive coil is connected to an electrode in an electrode assembly at a distal end of a pacing lead. Typically, a terminal member is molded or mounted within a flexure sleeve at the proximal end of the pacing lead and connected or joined to the proximal end of the conductive coil.

After the electrode assembly is positioned at a desired location within the heart, it is desirable to provide some method for securing the electrode assembly at that location. Mechanical fixation devices are used to firmly anchor the electrodes in the heart. One type of mechanical fixation device used is a corkscrew, or a helix electrode connector. During placement of the lead, the tip of the lead travels intravenously through veins and the heart. While traveling through the veins, the helix electrode connector at the tip of the lead may snag or attach to the side wall of the vein. Since this is highly undesirable as it may cause damage or other complications to a patient, retractable helixes are one of the optional constructions which have been provided for leads. In addition, temporary caps over the helix (such as an aqueous soluble cap, particularly a water soluble, innocuous organic material such as a sugar, starch or other biologically inert, or digestible material such as sugars, starches and the like (e.g., mannitol, sorbitol)) may be formed over the helix or tip. Preferably these materials are at least soluble or dispersible and preferably are inert or even digestible.

When using a retractable helix, the helix is extended and screwed into the heart muscle by applying a torque to the other end of the conductor without use of any further auxiliary device or with a special fixation stylet. A fixed or non-retractable helix electrode connector needs only to be positioned and secured to the heart muscle by the application of torque. Retractable helix designs employing special stylets are also available. If a soluble/dispersible cap is present on the helix, the cap must be given sufficient time to dissolve or disperse before complete securement of the helix electrode connector is attempted. A lead must be capable of being firmly secured into the wall of the cardiac tissue to prevent dislodgement therefrom, while avoiding perforation of the electrode completely through the cardiac tissue.

The pulse generator circuitry and power supply work in concert with the electrodes as a system which provides electrical pulses to the heart tissue. A low impedance electrode design may increase power delivery to the heart tissue, but at the same time, this higher energy usage results in shorter battery life. Shorter battery life is undesirable, since it increases the average number of surgical procedures to perform battery replacement for a patient.

There is a need for a body-implantable lead that has a helix for fixation to the wall of the atrium or ventricle of the heart. A separate desirable feature in body-implantable leads is for a lead having an electrode for positioning within the atrium or ventricle that allows for tissue ingrowth. Tissue ingrowth further enhances the electrical performance of the lead. The lead and electrode are further stabilized within the heart as a result of tissue ingrowth. Furthermore, there is a need for a relatively high pacing impedance electrode design which offers reasonable average voltage to the tissue. Such a high pacing impedance electrode would effectively reduce energy utilization and as a consequence, extend battery life.

It is also known to provide drugs to the patient's body before, during or after insertion of a lead or electrode. It is particularly well known to provide anti-inflammatants such as steroids, antibiotics, anti-fungal materials and the like in the region where the insertion has occurred. This is typically effected by implantation of a separate element which provides a drug (e.g., by elution from a carrier, dissolution from a slightly soluble mass, diffusion through a semi-permeable wall, slow release through a porous surface, or the like. A collar on a tip has also been reported in the literature as represented by the use of a steroid elution collar on the "Sweet Tip" Rx lead (CPI Guidant). In that embodiment, the entire drug delivery component is a collar which is fixed or slidably attached to the outside surface of the electrode or lead. This allows for the possibility of damage to the elution collar, in spite of care taken in packaging the lead.

SUMMARY OF THE INVENTION

According to the present invention, there is provided a body-implantable lead assembly comprising a lead. One end of the lead is adapted to be connected to electrical supply for providing or receiving electrical pulses. The other end of the lead comprises a distal tip (such as a helix) which is adapted to be connected to tissue of a living body. The lead is characterized by having either a) a porous electrode at the base of the helix and/or b) an insulating coating over a portion of the helix so that the impedance is increased for the helix as compared to a helix of the same size and materials without an insulating coating or porous electrode. The lead may also have an increased impedance or high impedance electrode which can act to extend the life of the battery. The high or at least the increased impedance electrode may be effected in any of a number of ways, including, but not limited to one or more of the following structures: 1) a fully insulated tissue-engaging tip (e.g., a helix) with an electrode at the base of the insulated tip, 2) a partially insulated engaging tip (only a portion of the surface area of the engaging tip being insulated), 3) a mesh or screen of material at the distal end of the lead, at the base of an extended engaging tip (whether a fixed or retractable tip), 4) the selection of materials in the composition of the mesh and/or tip which provide higher impedance, 5) the partial insulative coating of a mesh or screen to increase its pacing impedance, and 6) combinations of any of these features. There may be various other constructions to effect the high impedance, including the use of helical tips with smaller surface areas (e.g., somewhat shorter or thinner tips). There may also be a sheath of material inert to body materials and fluids and at least one conductor extending through a lumen of the lead body. The use of these various constructions in the tip also allows for providing the discharge from the tip in a more highly concentrated location or area in the tip.

According to one aspect of the present invention, there is provided a body-implantable lead assembly comprising a lead, one end being adapted to be connected to electrical supply for providing or receiving electrical pulses. The lead further comprises a distal tip which is adapted to be connected to tissue of a living body. The lead also has an electrode, especially a high impedance electrode intended to extend the life of the battery. There may be various constructions to effect the high impedance function. There may also be or alternatively be a sheath of material at the distal end of the lead assembly, with the sheath being inert to body materials and fluids and at least one conductor extending through the lead body.

The distal tip electrode is adapted, for example, for implantation proximate to the heart while connected with a system for monitoring or stimulating cardiac activity. The distal tip electrode includes an electrode tip, such as a helix (preferably with only a percentage of its entire surface area being electrically conductively exposed—only a portion of the surface is insulated—to increase its pacing impedance), preferably a mesh screen disposed at a distal end of the electrode tip, a fixation helix disposed within the electrode tip, in conjunction with a helix guiding mechanism. The mesh screen preferably is electrically active, and the area of the mesh screen and the percentage of electrically exposed surface area of the electrode tip can be changed to control its pacing impedance. Further, the mesh screen can entirely cover an end surface of the electrode tip, or a portion of the end surface in the form of an annular ring. In one embodiment, the helix guiding mechanism includes a hole punctured within the mesh screen. Alternatively, the helix guiding mechanism can include a guiding bar disposed transverse to a radial axis of the electrode. The helix is retractable, and is in contact with a movement mechanism. The movement mechanism provides for retracting the helix, such as during travel of the lead tip through veins. The helix is aligned with the radial axis of the electrode and travels through the guiding mechanism. The mesh may be tightly woven or constructed so that there are effectively no openings, or the mesh can be controlled to provide controlled porosity.

In another embodiment, the electrode tip includes a mesh screen forming a protuberance on the end surface of the electrode tip. The protuberance is axially aligned with the radial axis of the electrode. The helix travels around the protuberance as it passes through the mesh while traveling to attach to tissue within the heart. The helix also travels around the protuberance as it is retracted away from the tissue within the heart. If the mesh screen is sufficiently insulated around the protuberance, then a high pacing impedance tip is created. Advantageously, the protuberance allows for better attachment to the cardiac tissue without having the electrode tip penetrating or perforating therethrough.

Additionally, a distal tip electrode is provided including an electrode tip, a mesh screen disposed at a distal end of the electrode tip, a fixation helix disposed within the electrode tip, and a helix guiding mechanism. The electrode tip further may include a piston for moving the helix. The piston further may include a slot for receiving a bladed or fixation stylet. When engaged and rotated, the piston provides movement to the helix. The base provides a mechanical stop for the helix and piston when retracted back into the electrode tip.

In another embodiment, the distal tip assembly is adapted for implantation proximate to the heart while connected with a system for monitoring or stimulating cardiac activity. A fixation helix/piston assembly is housed by an electrode collar, housing, and base assembly. Attached to the proximal end of the helix is a piston which includes a proximal slot for receiving a bladed or fixation stylet. When a stylet is engaged in the slot and rotated, the piston provides movement to the helix. Depending on the embodiment, the fixation helix/piston assembly may be electrically active or inactive. The electrode collar, housing, and base all house the fixation helix/piston assembly. The proximal end of the electrode collar is attached to the distal end of the housing. Furthermore, the proximal end of the housing is attached to the distal end of the base, and the proximal end of the base is directly attached to the conductor coils of the lead.

A mesh screen may be attached to the distal tip of the electrode collar. The mesh screen, in another embodiment, is electrically active and serves as the electrode on the distal tip assembly. The tip (e.g., a helix) may then be fully insulated to increase the impedance of the tip or may be partially insulated (with preselected areas of the helix being insulated and other areas being non-insulated) to adjust the impedance of the tip to the specific or optimal levels desired. The area of the mesh screen can be modified to cover differing portions of the end surface of the distal tip assembly to control electrical properties of the lead. The fixation helix travels through a guiding mechanism, where the guiding mechanism allows the fixation helix to be extended and retracted. In one embodiment, the helix guiding mechanism includes a hole formed within the mesh screen. Alternatively, the helix guiding mechanism can include a guiding bar disposed transverse to a radial axis of the electrode collar. The mesh screen and/or guiding bar also serve as a full extension stop when the helix is fully extended. The base serves as a stop when the fixation helix/piston assembly is fully retracted.

The provided electrode tip supplies a retractable helix and a mesh screen which advantageously allows for sufficient tissue in-growth. The guide mechanism provides a convenient way to direct the rotation of the helix. A further advantage of the electrode tip is the provided mechanical stop. The mechanical stop aids in preventing over-retraction of the helix during the installation or removal of the electrode tip.

In yet another embodiment, the electrode uses a partially insulated fixation helix to provide a relatively high pacing impedance electrode. The fixation helix is insulated using insulating coatings over a portion of the fixation helix.

In combination with each of these high impedance tips, a drug delivery system is provided at least the majority of which drug delivery system is provided from a source within a volume which is within the structural walls of the lead and/or within a volume having its major dimensions and/or at least 50% of its volume generally within the projected area of the tip.

BRIEF DESCRIPTION OF THE DRAWINGS

FIG. 3A is a cross-sectional view of an electrode tip of a lead for monitoring and stimulating the heart with a drug delivery element constructed in accordance with one embodiment of the present invention.

FIG. 3B is an end view of the electrode tip of the lead shown in FIG. 3A.

DETAILED DESCRIPTION OF THE INVENTION

Figure 1:
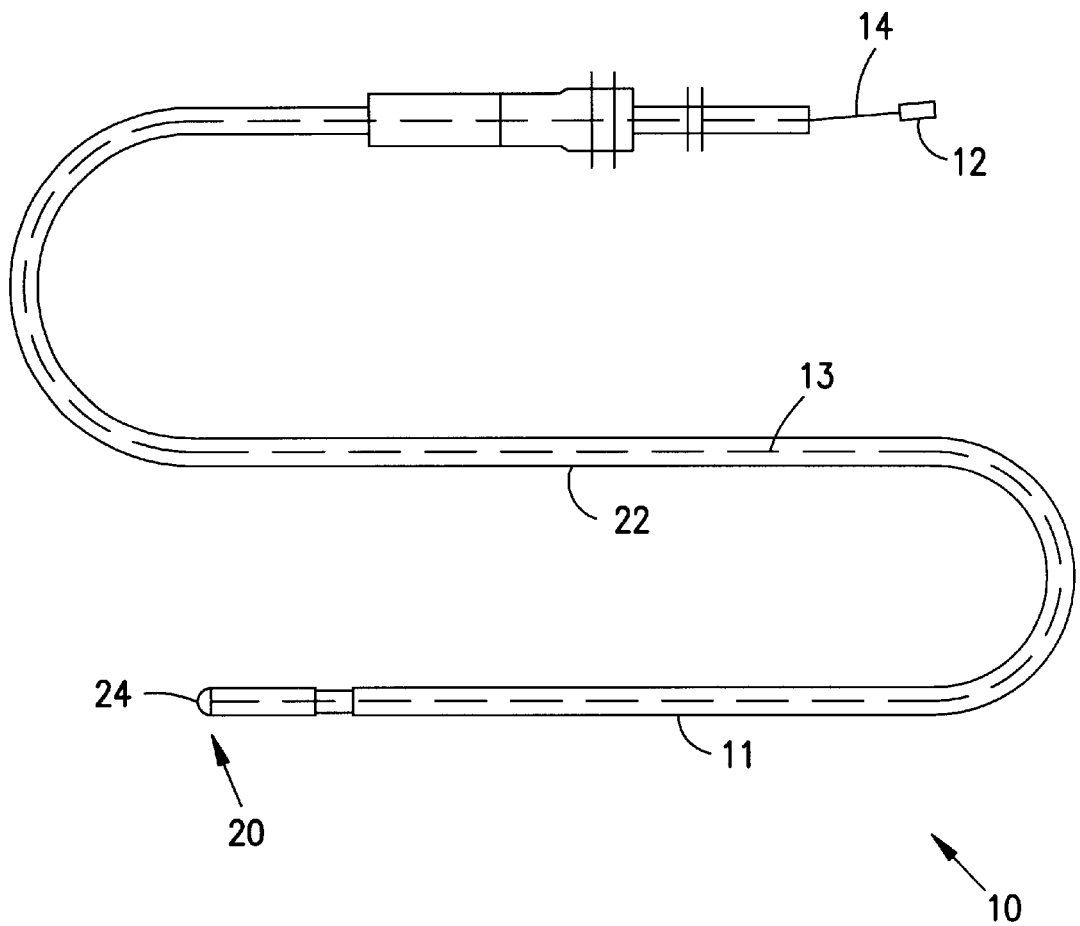
FIG. 1 is a first side elevational view illustrating a lead with a drug delivery element constructed in accordance with one embodiment of the present invention.

In the following detailed description, reference is made to the accompanying drawings which form a part hereof, and in which is shown by way of illustration specific embodiments in which specific aspects of the broader invention may be practiced. These embodiments are described in sufficient detail to enable those skilled in the art to practice both the broad concepts of the invention as well as more limiting specific constructions, and it is to be understood that other embodiments may be utilized and that structural changes may be made without departing from the spirit and scope of the present invention as disclosed herein. Therefore, the following detailed description is not to be taken in a limiting sense, and the scope of the present invention is defined by the appended claims.

As noted previously, there are a number of ways in which increased impedance may be effected for mechanically fastened electrode connections in atrial/ventricular implantable catheters (AVIC) systems. These include at least the following: 1) a fully insulated tissue engaging tip, such as a helix (at least with respect to all surfaces that are in electrical contact or electrically active physical relationship to heart muscles so that a pace would be effective if discharged at that portion of the tip), 2) a partially insulated engaging tip, such as a helix (only a portion of the surface area of the engaging tip being insulated, preferably there is sufficient coating so that there is at least 5%, or at least 10%, or at least 20 or 30%, or at least 40, 50 or 60%, or at least 70, 75, 80 or 90% of the surface area of the tip (e.g., the helix) which can discharge to heart muscle (or as percentages of the entire tip or as percentages of the entire helix that extends physically beyond the end plane of the catheter and which may therefore penetrate tissue or muscle)), 3) a porous, electrically conductive element, such as a mesh or screen of material at the proximal end of the helix or the distal end of the lead (excluding the helix), at the base of an extended engaging tip (such as the base of the extended helix, 4) the selection of materials in the composition of the mesh and/or tip (e.g., the helix) which provide higher impedance, 5) the partial insulative coating of a porous conductive element, such as the mesh or screen to increase its impedance, and 6) combinations of any of these features. There may be various constructions to effect the increased or high impedance, including the use of helical tips with smaller surface areas (e.g., somewhat shorter or thinner tips). There may also be other elements associated with the catheter and/or leads, such as a sheath of material inert to body materials and fluids, circuitry, microcatheters, and at least one conductor extending through the lead body.

In combination with each of these high impedance tips, a drug delivery system is provided at least the majority of which drug delivery system is provided from a source within a volume which is within the structural walls of the lead and/or within a volume having its major dimensions and/or at least 50% of its volume generally within the projected area of the tip.

The drug delivery element may comprise any of the various formats for drug delivery which are known for implantation, either temporary implantation or permanent implantation (usually defined as more than three days, but may include implantation for more than two weeks, more than two months, and more than two years). Such systems may include by way of non-limiting examples 1) a compacted tablet comprising more than 50% of the active ingredient (in association with such a structure or additives as to control the rate of release of the drug in contact with bodily fluids such as blood), 2) an absorbent material which controllably releases the drug in contact with bodily fluids (e.g., sponge-like materials, highly reticulated fibrous masses, cellular or foraminous structures such as foams, and the like), 3) solid masses with dispersed, dissolved or emulsified active ingredient which elutes, migrates, or dissolves from a carrier mass or continuous phase within the solid mass, and/or 4) encapsulated active ingredient which migrates through a porous or semipermeable shell or sheath, especially when the shell or sheath is in contact with bodily fluids. The shell or sheath may also be designed to be responsive to the pulses or side effects of the pulses (e.g., magnetic flux) so that its properties alter to increase or decrease the rate of release of the encapsulated active material. The components of the drug delivery element should comprise materials which can be tolerated by the body of a patient. Many natural binders or natural polymers with controlled properties may be advantageously used for this purpose, as may synthetic polymers, metals, composites and other natural materials. For example, binders which dissolve harmlessly within the body may include saccharides, polysaccharides, carbohydrates (including artificial and natural sugars and starches, including both d- and l-carbohydrates), gums, resins, harvested tissue, artificial tissue, fibrous masses (especially dense fibrous masses with a microporous structure), microporous film or masses, foraminous film or masses, reticulated film or masses, and other materials within these general classes such as polymers from the classes comprising polyurethanes, polyesters, polyethers, polyamides, polyolefins, polysiloxanes, silicone rubbers and elastomers, polyvinyl resins (e.g., polyvinyl alcohol, polyvinyl chloride, polyvinylidene chloride, polyvinyl acetals, polytetrafluoroethylene, etc.), cellulosic materials (both natural, modified and synthetic), metals (such as from Nitinol, titanium, stainless steel, etc.), and composites of these or other bio-acceptable materials. These compositions or elements may be provided as rods, sticks, threads, packets, shaped inserts, molded elements or the like in a location generally where the drug delivery system is provided so that at least the majority of the drug delivery system is within a volume which is within the structural walls of the lead and/or within a volume having its major dimensions and/or at least 50% of its volume generally within the projected area of the tip. This type of location is well exemplified in the Figures.

One aspect of the present invention with respect to the lead itself comprises an implantable electrode with a helical tip comprising:

an electrode having a distal end and a proximal end; and
a helix disposed within the electrode, which helix is aligned along a radial axis of the electrode towards the distal end, and which helix is either retractable or fixed; and
the implantable electrode having at least one feature selected from the group consisting of:
  a) the helix having a coating of an insulating material on its surface which covers at least 5% of its surface area but less than 95% of its surface area (which is exposed beyond the distal end of the electrode),
  b) the helix extending beyond the distal end of the electrode and the distal end of the electrode having a porous conductive surface at a base of the helix,
  c) a porous conductive element such as a screen or mesh at a base of the helix, which is retractable/extendable, with the helix being either active or inactive (electrically), and
  d) a partially insulated (partially insulation coated) porous conductive element (e.g., screen or mesh) at the base of an active or inactive, retractable/extendable or fixed helix.

The implantable electrode preferably has the helix with a coating of insulating material on its surface which covers from 5–100% (to 100% where there is an additional electrode element within the system) or 5–95% of surface area of the helix beyond the distal end of the electrode. Alternatively, the surface of the helix is that which is considered to be in electrically discharge-functional physical relationship with tissue or muscle into which it is embedded. For purposes of measuring or determining the distal end of the electrode, the tip extends beyond a tubular or cylindrical housing or structural portion which is considered the electrode, and the tip is an engaging portion that extends beyond the housing portion of the electrode. The distal end of the electrode is usually characterized as the end of the cylindrical housing or tubing carrying the tip, circuits, conductive elements, guides, etc. It is more preferred that the helix of the implantable electrode has a coating of insulating material on it surface which covers from 5–95% or 10–90% of the surface area of said helix beyond the distal end of the electrode. In combination with each of these high impedance tips, a drug delivery system is present, at least the majority of which drug delivery system is provided from a source within a volume which is within the structural walls of the lead and/or within a volume having its major dimensions and/or at least 50% of its volume generally within the projected area of the tip.

A lead 10 is illustrated in FIG. 1. The lead 10 comprises a lead body 11, an elongate conductor 13 contained within the lead body, and a lead tip 20 with an optional retractable tip assembly 24 contained in the lead tip 20. In addition, a stylet 14 is shown inserted into the lead body 11. A helix 100 (FIGS. 2A–5A), which consists of an electrical conductor coil, is contained in the retractable lead tip 24. In an alternative practice of the invention, the helix 100 extends and retracts by rotation of the stylet 14, as will be discussed further below. A Brady lead body is shown, although the invention could be incorporated with other leads, such as Tachy leads. The lead body 11 consists of electrical conductors 13 which are covered by a biocompatible insulating material 22. Polymers, such as silicone rubber, fluorinated resins, polyacrylates, polyamides ceramic or composite materials or other insulating material can be used for covering the lead body 11.

In one embodiment shown in FIGS. 3 and 3A, the helix 100 is formed of electrically conductive material offering low electrical resistance and also resistant to corrosion by body fluids. A biocompatible metal, such as titanium or platinum-iridium alloy is an example of a suitable material. Alternatively, the helix 100 is electrically inactive or insulated. In one embodiment, the helix 100 may be coated with an insulative material (not shown) or may be constructed of a rigid, corrosion resistant, non-electrically-conductive material (e.g., a ceramic). A housing 182, described in further detail below, is made from an electrically conductive material and covered with an insulating material such as a synthetic or natural polymer such as a silicone rubber. The housing 182 is directly connected to an electrical conductor within the lead 120. These materials are additionally suitable because they tend to be biologically inert and well tolerated by body tissue. Within the housing 182 is shown a packet 183 of microporous polypropylene with pores 185 having average dimensions of about 1–5 micrometers, and within said packet 183 is a fluid comprising steroid dissolved in a bio-acceptable organic solvent such as castor oil.

The helix 100 defines a lumen and thereby is adapted to receive a stiffening stylet 14 that extends through the length of the lead. The stylet 14 stiffens the lead 120, and can be manipulated to introduce an appropriate curvature to the lead, facilitating the insertion of the lead into and through a vein and through an intracardiac valve to advance the distal end of the lead 120 into the right ventricle of the heart (not shown). A stylet knob 154 is coupled with the stylet 14 for rotating the stylet 14 and advancing the helix 100 into tissue of the heart.

Figure 2B:
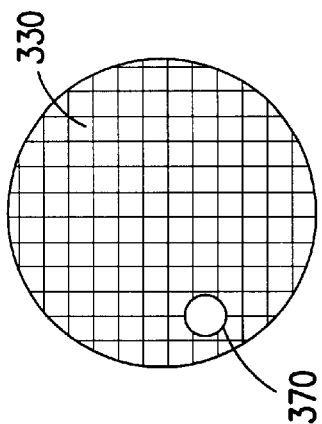
FIG. 2B is an end view of the electrode tip of the lead shown in FIG. 2A.
Figure 2A:
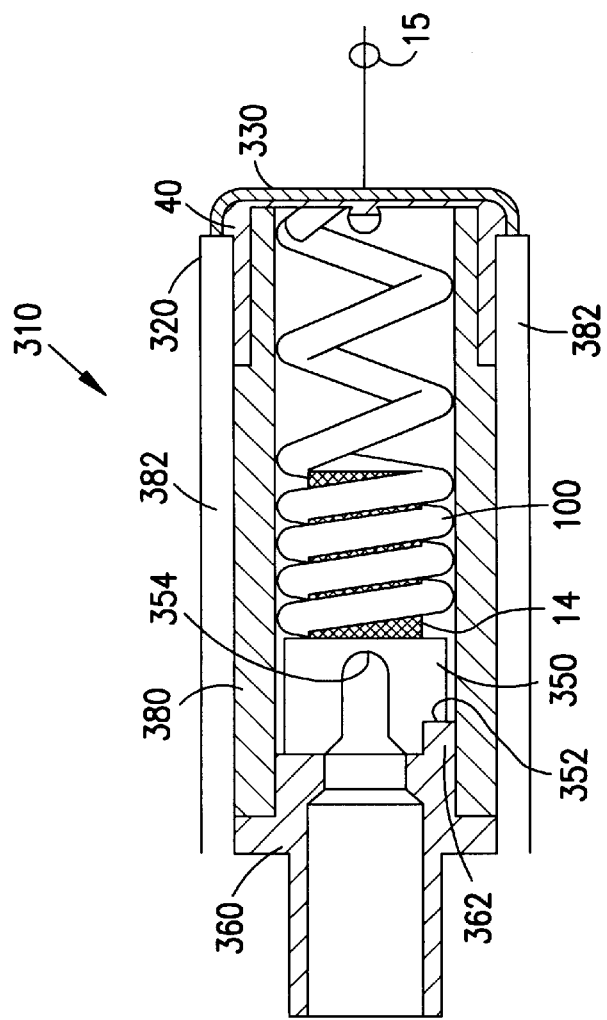
FIG. 2A is a cross-sectional view of an electrode tip of a lead for monitoring and stimulating the heart with a drug delivery element constructed in accordance with one embodiment of the present invention.

In one embodiment, as shown in FIGS. 2A and 2B, a lead 310 has an electrode tip 320 which is provided with a mesh screen 330. The mesh screen 330 completely encapsulates the diameter of the lead 310, and may serve, at least in part, as a pacing/sensing interface with cardiac tissue. If the helix 100 is electrically active, it too can help serve as a portion of a pacing or sensing interface. The mesh screen 330 is of a porous construction, preferably made of electrically conductive, corrosion resistant material. Using a mesh screen 330 having a porous construction allows for fibrotic ingrowth. This provides for a further anchoring of the lead tip 320 and also increases the sensing capability of the lead 310 by increasing the surface area in contact with the cardiac tissue. The mesh screen 330 may be attached to an electrode collar 40, which is electrically active. In a retractable catheter system, a housing 380, which is electrically conductive, encapsulates the piston 350 and the fixation helix 100. Insulation 382 is disposed about the housing 380 and collar 40. Behind the mesh screen 330 is located a disk-shaped mass 331 of porous polyurethane polymer having dispersed within the pores mannitol with a steroid (approximately 50% by weight of the mannitol) dispersed within the mannitol. As the outer surface of the mannitol dissolves, the dispersed steroid is released behind the mesh 330. Alternatively, the disk-shaped element could comprise gelatin which has the steroid dispersed therein, the gelatin having been crosslinked with non-toxic crosslinking agents to control its solubility and the rate of release of the steroid dispersed therein.

Disposed within the lead 310 is a lead fastener 100 for securing the lead 310 to cardiac tissue. The lead fastener 100 can be disposed along the radial axis 15 of the electrode lead 310. In this embodiment, the lead fastener comprises a fixation helix 100. The fixation helix 100 can be made electrically active or inactive as discussed above. Attached to the fixation helix 100 in a retractable tip system is a piston 350. The piston 350 is configured to mate with a bladed locking stylet 14 at a stylet slot 354, and acts as an interface between the stylet 14 and the helix 100. The stylet 14, coupled with the piston 350 at the stylet slot 354, extends and retracts the fixation helix 100 when the stylet 14 is rotated. The piston 350 can either be electrically active or inactive. The piston 350 also has a slot 352, which allows the piston 350 to mate with a base 360.

Fitted with a knob 362, as shown in FIG. 2A, the base 360 mates with the slot 352 of the piston 350. The base 360 serves as a stop once the fixation helix 100 is fully retracted. The electrically conductive base 360 also allows passage of a bladed locking stylet 14 and attachment of electrode coils (not shown).

In addition, the lead 310 has a guide groove 370. The groove 370 is formed by puncturing a hole (not shown) within the mesh screen 330, although the guide groove 370 can be formed by other methods known by those skilled in the art. Having a circular cross-section, the guide groove 370 may have a diameter greater than that of the conductor forming the helix 100. The groove 370 is disposed within the mesh screen 330, and directs the fixation helix 100 from its retracted position, as illustrated in FIG. 2A, to an extended position (not shown). The groove 370 also reversibly directs the fixation helix 100 from an extended position to the retraction position.

In a second embodiment, as shown in FIGS. 3A and 3B, a lead 110 has an electrode tip 120 which is provided with a mesh screen 130. The mesh screen 130 completely encapsulates the diameter of the lead or electrode tip 120, and serves as the pacing/sensing interface with cardiac tissue. The screen 130 is of a porous construction, made of electrically conductive, corrosion resistant material. Using a mesh screen 130 having a porous construction allows for fibrotic ingrowth. This provides for a further anchoring of the lead tip 120 to tissue and also increases the sensing capability of the lead 110. The sensing capability is enhanced because the mesh screen 130 has more surface area than corresponding solid material. The ingrowth of fibrotic tissue into the mesh screen 130 increase the sensing capability of the lead 110 by increasing the surface area in contact with the cardiac tissue. If the cross-section or effective area of the tip 120 were extended down the length of the lead 110 and past the drug delivery element 183, the outer dimension of the tip 120 would enclose more than 50% by volume of the drug delivery composition. In this case, approximately 100% of the drug delivery material would be encompassed by the volume traversed by the outer dimension of the tip 120. Furthermore, the geometry of the mesh screen 130, particularly any protuberance, as will be discussed below, creates a high pacing impedance tip. The outer dimension of the screen 130 may alternatively be used to define the outer dimensions of the drug delivery device or at least 50% of the volume of the drug delivery element.

The mesh screen 130 may form a protuberance 135 from a flat edge portion 137 of the mesh screen 130 in a generally central portion of the electrode tip 120. The protuberance 135 may be generally circular in cross-section, but may be any shape (e.g., truncated cylindrical, truncated pyramidal, oval, ellipsoidal, etc.) as a result of design or circumstance which provides a flat or conformable surface (preferably not a rigid, sharp face which will not conform to tissue) abutting tissue, and preferably has a diameter smaller than a diameter of the lead 110. In addition, the protuberance 135 is aligned with the radial axis 15 of the lead 110. Metallurgically bonded (or otherwise secured or fastened) to an electrode collar 40, a process known by those skilled in the art, the mesh screen 130 is attached to the electrode tip 120. The electrode collar 40 is electrically active. The projected diameter or surface area of the cross-section 139 of the helix 100 is shown to be broader or wider than the cross-section 141 of the drug delivery element 183.

Disposed within the electrode lead 110 is a lead fastener for securing the electrode lead 110 to cardiac tissue. The lead fastener can be disposed along the radial axis 15 of the electrode lead 110. In this embodiment, the lead fastener comprises a fixation helix 100. The fixation helix 100 can be made electrically active or inactive to change sensing and pacing characteristics, as discussed above. Attached to the fixation helix 100 is a piston 150. At the base of the piston 150 is shown a porous metal casement or cage or mesh 151 containing microcapsules 153 with a fill of steroid. The microcapsules 153 are made from coacervated gelatin. The microcapsules 153 may have a range of different release properties so that the rate of release of the steroid may be controlled. The piston 150 is configured to mate with a bladed locking stylet 14, thereby providing a movement assembly. The stylet 14 extends and retracts the fixation helix 100 when the stylet 14 is rotated. The piston 150 can either be electrically active or inactive. The piston 150 also has a slot 152. The slot 152 of the piston 150 allows the piston 150 to mate with a base 160 upon full retraction. As can be seen in this construction, although the drug delivery system is fully contained within or as part of the housing 182 and frame 180 of the lead 210, portions of the drug delivery element may extend beyond the diameter of the helix 100.

The base 160 is modified with a knob 162 to mate with the slot 152 of the piston 150. The knob 162 mates with the piston 150 to prevent over-retraction once the helix 100 has been fully retracted. The stylet 14 operates to advance the fixation helix 100. As the implanter rotates the stylet 14, the stylet 14 engages the piston 150 at the stylet slot 154 and rotates the piston 150, which moves the fixation helix 100 through a guide groove 170. The guide groove 170 is for ensuring that the fixation helix 100 is properly guided out of and into the end of the electrode. Once the fixation helix 100 is fully retracted, the base 160 serves as a mechanical stop. The base 160 also allows passage of a bladed locking stylet 14 and attachment of electrode coils. Additionally, the base 60 is electrically active.

The electrode lead 110 also has a guide groove 170. The groove 170 is formed by puncturing a hole within the mesh screen. Having a circular cross-section, the groove 170 has a diameter greater than that of the conductor forming the helix 100. The groove 170 is disposed within the mesh screen 130, and directs the fixation helix 100 from its retracted position, as illustrated in FIG. 2A, to an extended position (not shown). During implantation, after the electrode is in contact with tissue at the desired location in the heart, the stylet 14 is rotated which causes the piston to advance the fixation helix out of the groove 170. As the fixation helix 100 is placed in an extended position, the helix 100 travels through groove 170 and circles around the protuberance 135. The groove 170 also directs the fixation helix 100 from an extended position to the retracted position. Advantageously, the mesh screen 130 prevents the implanter from overextension and advancing the helix 100 too far into the tissue. An electrically conductive housing 180 encapsulates both the piston 50 and the fixation helix 100. Insulation 182 covers the housing 180, the collar 40, and a portion of the mesh screen 130. The insulation 182 over the mesh screen 130 controls the impedance of the electrode tip 120.

Figure 4B:
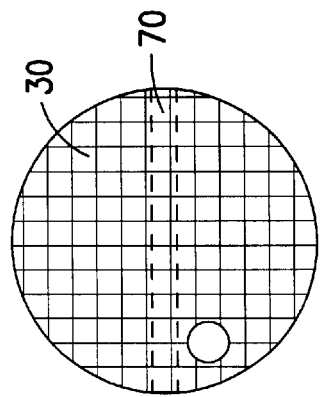
FIG. 4B is an end view of the electrode tip of the lead shown in FIG. 4A.
Figure 4A:
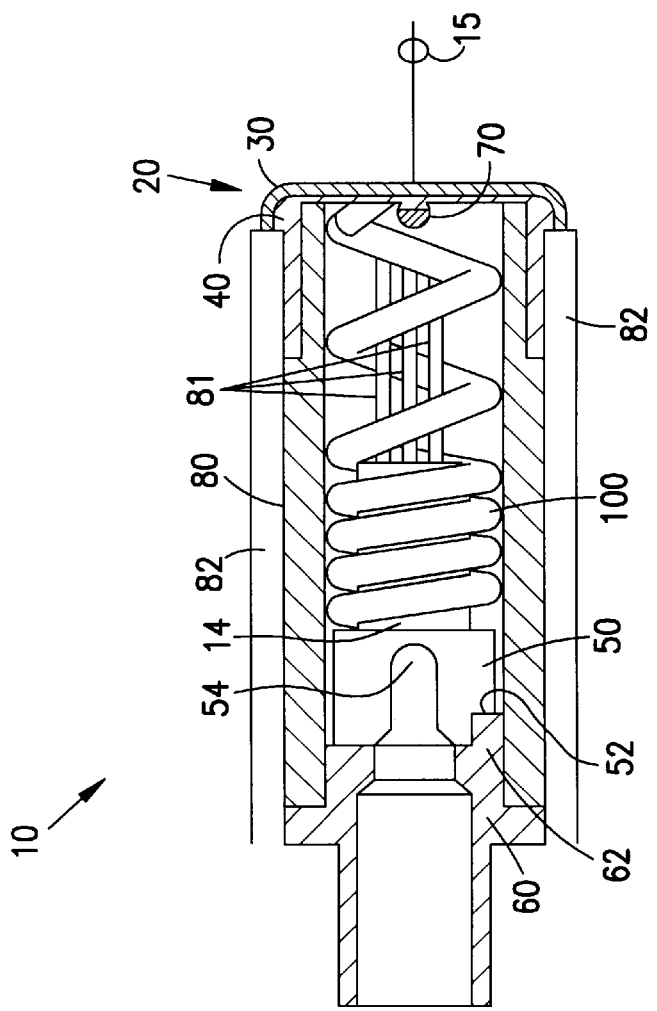
FIG. 4A is a cross-sectional view of an electrode tip of a lead for monitoring and stimulating the heart with a drug delivery element constructed in accordance with one embodiment of the present invention.

In a third embodiment as shown in FIGS. 4A and 4B, a lead 10 has an electrode tip 20 which is provided with a mesh screen 30. The mesh screen 30 completely encapsulates the diameter of the lead tip. Metallurgically bonded (or otherwise secured, adhered or fastened) to an electrode collar 40, the mesh screen 30 is attached to the electrode tip 20. The electrode collar 40 is electrically active. A housing 80 is disposed about the helix 100, and is electrically active. Insulation 82, encompasses the housing 80 and collar 40. Within the volume defined by the insulation 82 and the housing 80 is a series of rods 81 of varying thickness secured to the piston 50, within which rods 81 are dispersed particulate steroid material or within which rods 81 are dissolved steroid material which elutes from the rods 81 when the rods are in contact with body fluids, such as blood. The steroid may actually be selected to be only marginally compatible with the composition of the rods 81 so that the steroid will bloom or exude from the rods 81 without the necessity of being leached by fluids, but may then be merely carried away by the fluids or contact with solid tissue.

In one embodiment, as shown in FIGS. 2A and 2B, a lead 310 has an electrode tip 320 which is provided with a mesh screen 330. The mesh screen 330 completely encapsulates the diameter of the lead, and serves as the pacing/sensing interface with cardiac tissue. If the helix is electrically active, it too can help serve as a pacing or sensing interface. The mesh screen 330 is of a porous construction, made of electrically conductive, corrosion resistant material. Using a mesh screen 330 having a porous construction allows for fibrotic ingrowth. This provides for a further anchoring of the lead tip 320 and also increases the sensing capability of the lead 310 by increasing the surface area in contact with the cardiac tissue. The mesh screen 330 is attached to an electrode collar 40, which is electrically active. A housing 380, which is electrically conductive, encapsulates the piston 350 and the fixation helix 100. Insulation 382 is disposed about the housing 380 and collar 40.

Disposed within the lead 310 is a lead fastener for securing the lead 310 to cardiac tissue. The lead fastener can be disposed along the radial axis 15 of the electrode lead 310. In this embodiment, the lead fastener comprises a fixation helix 100. The fixation helix 100 can be made electrically active or inactive as discussed above. Attached to the fixation helix 100 is a piston 350. The piston 350 is configured to mate with a bladed locking stylet 14 at a stylet slot 354, and acts as an interface between the stylet 14 and the helix 100. The piston 350 is itself comprised of a porous material into which a therapeutically active drug has been imbibed or dispersed during manufacture of the piston 350. The stylet 14, coupled the piston 350 at the stylet slot 354, extends and retracts the fixation helix 100 when the stylet 14 is rotated. The piston 350 can either be electrically active or inactive. The piston 350 also has a slot 352, which allows the piston 350 to mate with a base 360.

Fitted with a knob 362, as shown in FIG. 2A, the base 360 mates with the slot 352 of the piston 350. The base 360 serves as a stop once the fixation helix 100 is fully retracted. The electrically conductive base 360 also allows passage of a bladed locking stylet 14 and attachment of electrode coils. The drug would elute from the piston 350 and exit through the screen 330 into the patient.

In addition, the lead 310 has a guide groove 370. The groove 370 is formed by puncturing a hole within the mesh screen, although the guide groove can be formed by other methods known by those skilled in the art. Having a circular cross-section, the groove 370 has a diameter greater than that of the conductor forming the helix 100. The groove 370 is disposed within the mesh screen 330, and directs the fixation helix 100 from its retracted position, as illustrated in FIG. 2A, to an extended position (not shown). The groove 370 also directs the fixation helix 100 from an extended position to the retraction position.

In a second embodiment, as shown in FIGS. 3A and 3B, a lead 110 has an electrode tip 120 which is provided with a mesh screen 130. The mesh screen 130 completely encapsulates the diameter of the lead tip, and serves as the pacing/sensing interface with cardiac tissue. The screen 130 is of a porous construction, made of electrically conductive, corrosion resistant material. Using a mesh screen 130 having a porous construction allows for fibrotic ingrowth. This provides for a further anchoring of the lead tip 120 and also increases the sensing capability of the lead 110. The sensing capability is enhanced because the mesh screen 130 has more surface area than corresponding solid material. The ingrowth of fibrotic tissue into the mesh screen 130 increase the sensing capability of the lead 110 by increasing the surface area in contact with the cardiac tissue. Furthermore, the geometry of the mesh screen, particularly the protuberance, as will be discussed below, creates a high pacing impedance tip.

The mesh screen 130 forms a protuberance 135 from a flat edge portion 137 of the mesh screen 130 in a generally central portion of the electrode tip 120. The protuberance 135 is generally circular in cross-section, and has a diameter smaller than a diameter of the lead 110. In addition, the protuberance 135 is aligned with the radial axis 15 of the lead 110. Metallurgically bonded to an electrode collar 40, a process known by those skilled in the art, the mesh screen 130 is attached to the electrode tip 120. The electrode collar 40 is electrically active.

Disposed within the electrode lead 110 is a lead fastener for securing the electrode lead 110 to cardiac tissue. The lead fastener can be disposed along the radial axis 15 of the electrode lead 110. In this embodiment, the lead fastener comprises a fixation helix 100. The fixation helix 100 can be made electrically active or inactive to change sensing and pacing characteristics, as discussed above. Attached to the fixation helix 100 is a piston 150. The piston 150 is configured to mate with a bladed locking stylet 14, thereby providing a movement assembly. The stylet 14 extends and retracts the fixation helix 100 when the stylet 14 is rotated. The piston 150 can either be electrically active or inactive. The piston 150 also has a slot 152. The slot 152 of the piston 150 allows the piston 150 to mate with a base 160 upon full retraction.

The base 160 is modified with a knob 162 to mate with the slot 152 of the piston 150. The knob 162 mates with the piston 150 to prevent over-retraction once the helix 100 has been fully retracted. The stylet 14 operates to advance the fixation helix 100. As the implanter rotates the stylet 14, the stylet 14 engages the piston 150 at the stylet slot 154 and rotates the piston 150, which moves the fixation helix 100 through a guide groove 170. The guide groove 170 is for ensuring that the fixation helix 100 is properly guided out of and into the end of the electrode. Once the fixation helix 100 is fully retracted, the base 160 serves as a mechanical stop. The base 160 also allows passage of a bladed locking stylet 14 and attachment of electrode coils. Additionally, the base 60 is electrically active.

The electrode lead 110 also has a guide groove 170. The groove 170 is formed by puncturing a hole within the mesh screen. Having a circular cross-section, the groove 170 has a diameter greater than that of the conductor forming the helix 100. The groove 170 is disposed within the mesh screen 130, and directs the fixation helix 100 from its retracted position, as illustrated in FIG. 2A, to an extended position (not shown). During implantation, after the electrode is in contact with tissue at the desired location in the heart, the stylet 14 is rotated which causes the piston to advance the fixation helix out of the groove 170. As the fixation helix 100 is placed in an extended position, the helix 100 travels through groove 170 and circles around the protuberance 135. The groove 170 also directs the fixation helix 100 from an extended position to the retracted position. Advantageously, the mesh screen 130 prevents the implanter from overextension and advancing the helix 100 too far into the tissue. An electrically conductive housing 180 encapsulates both the piston 50 and the fixation helix 100. Insulation 182 covers the housing 180, the collar 40, and a portion of the mesh screen 130. The insulation 182 over the mesh screen 130 controls the impedance of the electrode tip 120.

In a third embodiment as shown in FIGS. 4A and 4B, a lead 10 has an electrode tip 20 which is provided with a mesh screen 30. The mesh screen 30 completely encapsulates the diameter of the lead tip. Metallurgically bonded to an electrode collar 40, the mesh screen 30 is attached to the electrode tip 20. The electrode collar 40 is electrically active. A housing 80 is disposed about the helix 100, and is electrically active. Insulation 82, encompasses the housing 80 and collar 40.

Disposed within the lead 10 is a lead fastener for securing the lead 10 to cardiac tissue. The lead fastener can be disposed along the radial axis 15 of the lead 10. In this embodiment, the lead fastener comprises a fixation helix 100. The fixation helix 100 can be made electrically active or inactive to change sensing and pacing characteristics.

The helix 100 is of a well known construction. Using a conductor coil such as helix 100 has been shown to be capable of withstanding constant, rapidly repeated flexing over a period of time which can be measured in years. The helix 100 is wound relatively tightly, with a slight space between adjacent turns. This closely coiled construction provides a maximum number of conductor turns per unit length, thereby providing optimum strain distribution. The spirally coiled spring construction of helix 100 also permits a substantial degree of elongation, within the elastic limits of the material, as well as distribution along the conductor of flexing stresses which otherwise might be concentrated at a particular point.

Attached to the fixation helix 100 is a piston 50. The piston 50 is configured to mate with a bladed locking stylet 14. The piston 50 advances the fixation helix 100 once the lead is placed in position within the heart. The piston 50 can either be electrically active or inactive. The piston 50 also has a slot 52 and a stylet slot 54. The stylet 14 couples with the stylet slot 54 and extends or retracts the fixation helix 100 when the stylet 14 is rotated. The slot 52 of the piston 50 allows the piston 50 to mate with a base 60 when the helix 100 is retracted to prevent over retraction. The base 60 is configured with a knob 62 to mate with the slot 52 of the piston 50. Once the fixation helix 100 is fully retracted, the base 60 serves as a stop at full retraction. The base 60 also allows passage of a bladed locking stylet 14 and attachment of electrode coils. In addition, the base 60 is electrically active.

The lead 10 also includes a guiding bar 70. Extending across the diameter of the tip, the guiding bar 70 is generally cylindrical in shape. The guiding bar 70 directs the fixation helix 100 from its retracted position, as illustrated in FIG. 2A, to an extended position (not shown) as the piston 52 advances the helix 100. The guiding bar 70 also directs the fixation helix 100 as it is retracted from an extended position to the retraction position through the mesh screen. Although a guiding bar 70 is described, other types of guiding mechanisms can be used such as helical passageways, threaded housings, springs, and are considered within the scope of the invention. Additionally, the lead 10 is provided with a seal (not shown) for preventing entry of body fluids and tissue from entering the lead through the opening therein. The seal could be a puncture seal between the piston 50 and the base 60. Alternatively, O-rings could be used to seal the electrode.

Figure 5B:
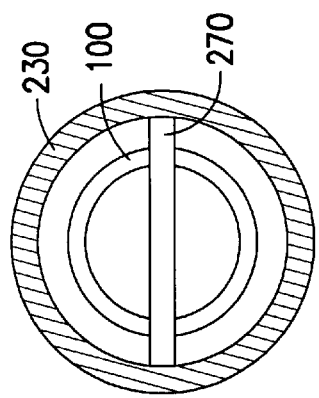
FIG. 5B is an end view of the electrode tip of the lead shown in FIG. 5A.
Figure 5A:
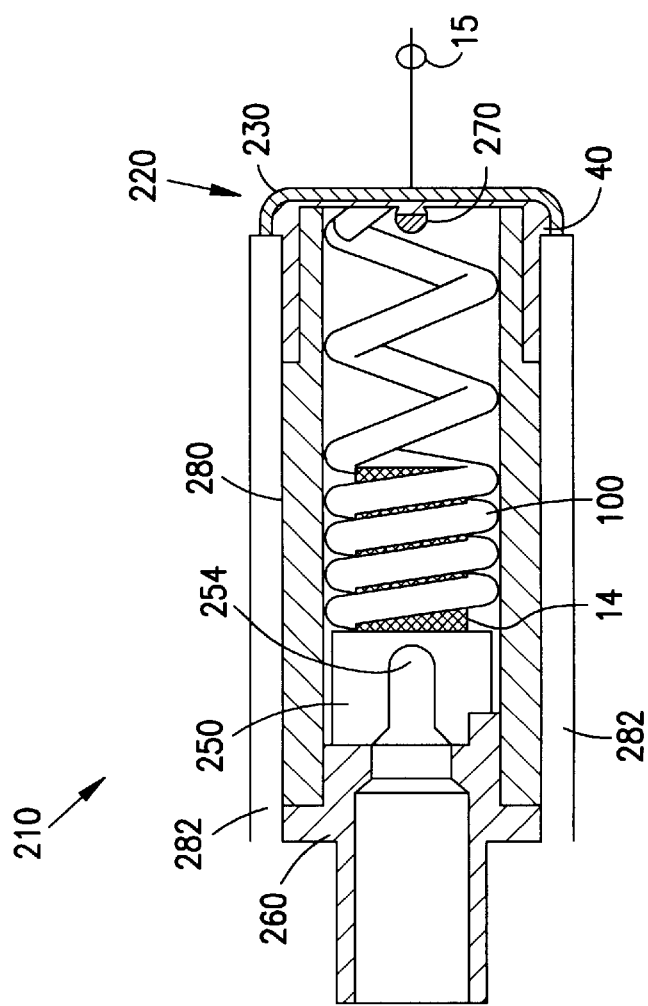
FIG. 5A is a cross-sectional view of an electrode tip of a lead for monitoring and stimulating the heart with a drug delivery element constructed in accordance with one embodiment of the present invention

In a fourth embodiment as shown in FIGS. 5A and 5B, a lead 210 has an electrode tip 220 which is provided with a mesh screen 230. The mesh screen 230 forms an annular ring having an open center, where the annular ring is centered at a radial axis 15 of the electrode lead 210. The mesh screen 230 provides more surface area than a smooth tipped electrode which aids in sensing. The removal of the center portion of the mesh screen creates a high impedance pacing tip due to the nature of the surface geometry. Metallurgically bonded, formed from sintered particles, fused, bonded, adhesively secured or mechanically attached to an electrode collar 40, the mesh screen 230 is attached to the electrode tip 220. The electrode collar 40 is electrically active.

Disposed within the lead 210 is a lead fastener for securing the lead 210 to cardiac tissue. The lead fastener can be disposed along the radial axis 15 of the electrode lead 210. In this embodiment, the lead fastener comprises a fixation helix 100. The fixation helix 100 can be made electrically active or inactive as discussed above. Attached to the fixation helix 100 is a piston 250. The piston 250 has a stylet slot 254 and is configured to mate with a bladed locking stylet 14. The stylet 14, coupled with the piston 250 at the stylet slot 254, extends and retracts the fixation helix 100 when the stylet 14 is rotated. The piston 250 can either be electrically active or inactive. The base 260 serves as a stop once the fixation helix 100 is fully retracted. The base 260 also allows passage of a bladed locking stylet 14 and attachment of electrode coils. The base 60 is electrically active.

Additionally, the electrode lead also has a guiding bar 270. The guiding bar 270 directs the fixation helix 100 from its retracted position, as illustrated in FIGS. 5A and 5B, to an extended position (not shown). The guiding bar 270 also directs the fixation helix 100 from an extended position to the retracted position. Although a guiding bar 270 has been described, other types of mechanisms could be used to extend the helix, and are considered within the scope of the invention. A housing 280 encapsulates the piston 250 and the fixation helix 100, and insulation 282 is disposed over the housing 280 and collar 40. Although not a preferred embodiment, the housing 280 itself or in combination with a second drug delivery device, here shown as a porous stylet 14, may be part or all of the drug delivery system. By having the walls of the housing 280 elute drug and the stylet 14 elute drug, no redesign of the structure would have to be made, but only construction materials would have to be replaced during the construction of the elements for the cathode/lead.

Insulation generally covers the housing, the collar, and a portion of the electrical discharge surface (e.g., the cathode, the helix and/or the porous material or mesh). The insulation over the mesh screen further controls the impedance of the electrode tip. The insulated coating, whether present on the helix or the mesh or other elements which are potentially electrically active or on which electrical activity is to be suppressed, should be biocompatible, non-thrombogenic, and otherwise safe for implantation. The insulation coating should be of dimensions which effect the insulation, increase the pacing impedance (where desired), but which dimensions do not interfere with the performance of the tip, the lead or the helix or the health of the patient. The insulation is present as a coating (a material which tends to conform to the surface rather than completely reconfigure it, as would a lump of material). The coating usually should be at least 0.5 microns in thickness, usually between 0.5 and 100 microns, preferably between 1.0 and 30 or 50 microns, more preferably between 1 and 20 microns, still more preferably between 1.5 and 15 microns, and most preferably between 1.5 or 2.0 microns and 10 or 15 microns. The coating may be provided by any convenient process, such as simple placement of a thin-walled tubing, electrophoretic deposition, dip coating, spin coating, in situ polymerization, vapor deposition, sputtering and the like. Any insulating material is useful, such as polymers, ceramics, glasses, and the like, but because of their convenience in application, flexibility and availability, polymers are preferred. Polymers from such classes as polyesters, polyamides, polyurethanes, polyethers, polysiloxanes, polyfluorinated resins, polyolefins, polyvinyl polymers, polyacrylates (including polymethacrylates), and the like may be used with various leads and tips according to the practice of the present invention. Parylene is a preferred material, as described herein, with a thickness of between 1.5 and 10 microns.

In yet another embodiment, a partially insulated fixation helix is used to provide a relatively high impedance electrode design. Leads comprising a distal or electrode end and a proximal or connector end may be used. A "miniature" wire-in-basket porous electrode may be metallurgically bonded (or otherwise fastened, adhered or secured) upon the distal end of a metallic pin, provided with a blind hole. Circumferential to this subassembly, a sharpened wire fixation helix may be positioned and attached at a general location proximal to the electrode by any convenient means which allows electrical continuity. This attachment includes, but is not limited to, crimping, spot welding, laser welding, the use of grooves upon the surface of the pin, the use of thin metallic overband (also not shown) or any combination thereof. A portion of this fixation helix is provided with an extremely thin layer of a biostable, biocompatible polymer, which, inter alia, provides electrical insulation between the fixation helix and the cardiac tissue. In one embodiment, the insulated portion is the majority of the fixation helix, leaving a relatively small uninsulated region of fixation helix. This approach offers increased impedance to reduce energy dissipation in pulsing functions, such as pacing functions. Other varying embodiments include, but are not limited to, a portion which is approximately or substantially equal to half of the fixation helix, and a portion which is approximately or substantially equal to a minority of the fixation helix. Such embodiments provide different amounts of uninsulated region and different amounts of impedance. The thin coating of electrically insulating coating must usually be at least 1 micron in thickness to provide a significant insulating effect, depending upon its insulating ability and properties. The thickness of the coating is limited primarily by physical limitations on the system. The coating can not be so thick as to interfere with the fastening ability of the helix or to increase the size of the helix beyond that which is tolerable for the use of the helix and the patient. Typically, the coating is at least one micron up to about 100 microns, more typically the coating is between 1 and 30 microns, preferably between 1.5 and 20 microns, more preferably between 1.5 and 15 microns, and most preferably between 2 and 10 microns. The material used for the coating should, of course, be biocompatible and even more preferably non-thrombogenic. Materials such as Parylene™, polyurethanes, polyacrylates (including polymethacrylates), polyesters, polyamides, polyethers, polysiloxanes, polyepoxide resins and the like can be used. Crosslinked polymers within these classes may be preferred for their resistance to breakdown and their physical durability. As the coating is to be maintained within the body of a recipient, the coating composition should not be water-soluble or aqueous soluble within the parameters and environment encountered within animal bodies (e.g., it should not be soluble within blood, serum or other body fluids with which it might come into contact).

To the proximal end of this pin, a metallic conductor coil may be conveniently attached to provide electrical connection to the implantable pacemaker (not shown) by means of a connector. In one embodiment, local (e.g., steroid or other medicinal) therapy is provided by a (e.g., circumferential) steroid/polymer matrix positioned immediately proximal to the porous electrode. In one embodiment, the circumferential steroid/polymer matrix is provided with a distal taper. Other embodiments include other distal configurations, including, but not limited to, non-tapered or "inflated" configurations. In one embodiment, an internalized, medicinal or biologically active (e.g., steroid) releasing matrix is used. Proximal to this biologically active (e.g., steroid) eluting matrix, a generally cylindrical polymeric tubing (this is the preferred shape, but the shape is a matter of choice) 820 is used to provide electrical insulation of this entire assembly. In one embodiment, the lead is "unipolar." In one embodiment, an ablative protective covering positioned over the entirety of distal end is used (not shown). One example of such a covering is the mannitol "Sweet Tip"® electrode of Guidant Corporation's Rhythm Management group. In one embodiment, a "bipolar" lead is provided with the distal electrode features described.

During an in vitro evaluation of this electrode design, polymeric coatings intended to partially insulate the fixation helix were prepared and evaluated. In one embodiment, the Parylene coating is extremely thin (~3μ), providing a coating with uniform coverage which is adherent to the metallic substrate, and which is controllable to provide an abrupt margin. The silicone rubber coating is known to be somewhat thicker (~10μ), uniform in coverage, somewhat less adherent to the metallic substrate, and controllable to an abrupt margin. Other coatings may be used without departing from the spirit and scope of the present invention.

The Parylene or other insulative coating effectively increases in vitro "pacing impedance." Application of a non-continuous or partially extensive coating of an electrically insulating polymer such as Parylene to the metallic fixation helix produces the desired increase in impedance compared to an uninsulated helix as well as other existing designs. For example, it has been demonstrated that one embodiment using a coated fixation helix provides a pacing impedance of over approximately 800 ohms which is larger than the impedance of some electrodes using an uncoated fixation helix. The post-implant pacing impedance of an embodiment using a coated fixation helix remains higher than that of typical electrodes using an uncoated fixation helix. In one experiment, a coated fixation helix using Parylene as an insulating layer provided over 1200 ohms average pacing impedance on the day of implantation and over 900 ohms ten days after the implant.

Additionally, post-implant average voltage threshold of the Parylene insulated miniaturized electrode is less than the other high impedance electrodes. Such performance is considered to be desirable. In one experiment, an embodiment with a coated fixation helix having a voltage threshold of approximately 0.2 volts on the day of implant was measured at about 0.7 volts at ten days after the implant (using a 0.5 ms pulse width). An electrode with an uncoated fixation helix demonstrated over 0.8 volts average voltage threshold at ten days after the implant, illustrating the benefits of the coated fixation helix.

An additional benefit is that the coated fixation helix embodiments may provide an improvement in both the implant as well as post-implant average S-wave amplitude detection.

The miniaturized high impedance, positive fixation porous electrode technology described here provides the following advantages over the prior art. For one example, the coated fixation helix embodiments provide an electrode where the benefits of high impedance pacing are realized through downsizing the porous electrode and insulating the fixation helix. Downsizing of the porous electrode may be accomplished, for example, by having a smaller porous (e.g., mesh) electrode supported on a non-conductive surrounding support element (e.g., a polymeric or composite film with a mesh central area, particularly a mesh truncated conical or pyramidal area of flexible, conductive mesh). An area of the completely conductive mesh may also be discontinuously coated leaving a conductive central or conductive raised area, particularly surrounding a contact, engaging element, or helix. Further, an external steroid collar provides a fabrication advantage since such a component can be readily mass produced compared to smaller components with elaborate profiles. Still further, fabrication of a lead with this external collar is streamlined. The higher impedance design conserves battery power to provide longer battery life with fewer battery replacements. Other benefits exist which are not described in detail herein, however, which those skilled in the art will appreciate.

Figure 6:
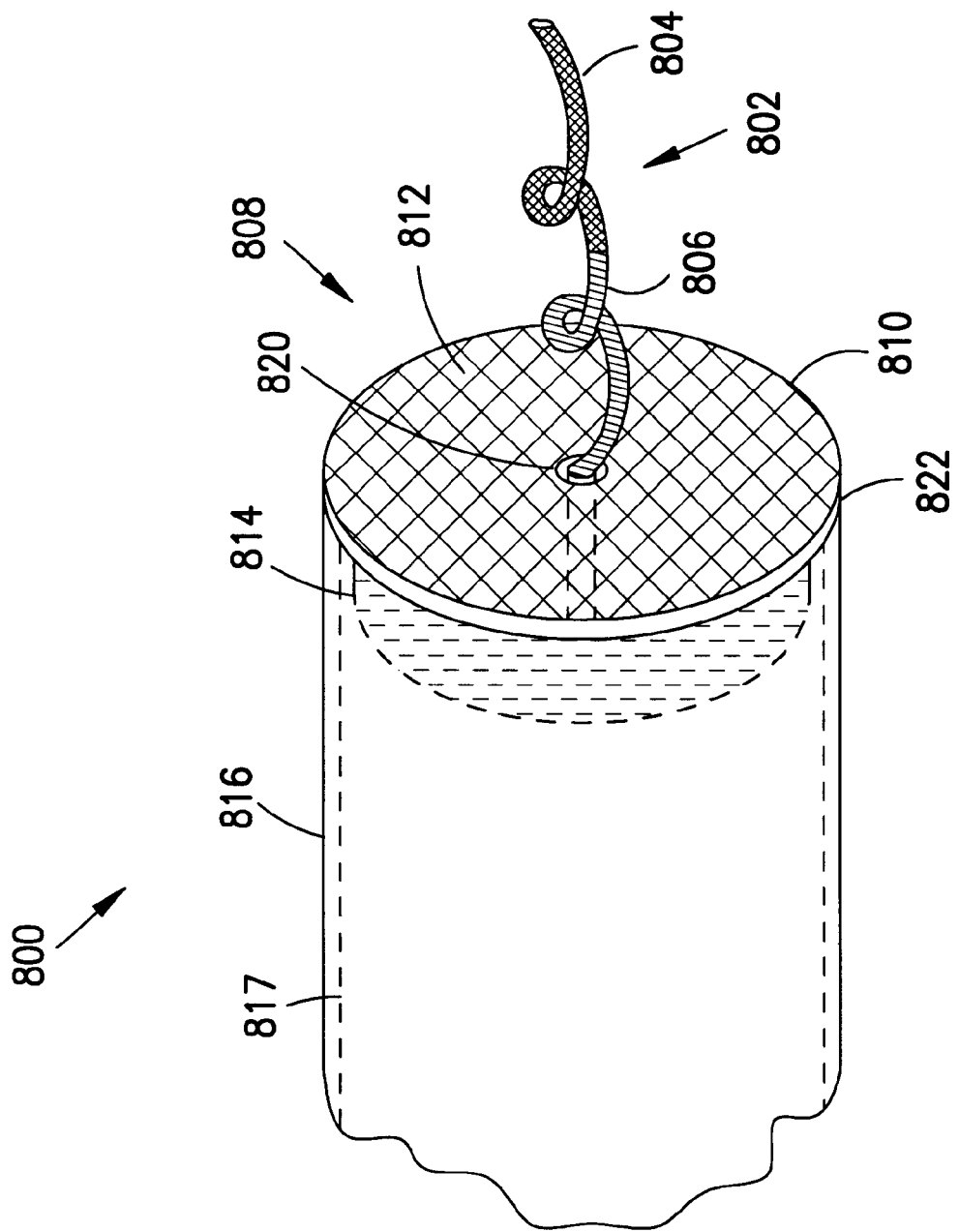
FIG. 6 shows a partially insulated helical tip with a drug delivery element according to the present invention which increases the impedance of the tip as compared to a fully non-insulated helical tip.

FIG. 6 shows a high impedance catheter tip 800 with a partially insulated tip 802 and a partially insulated mesh 808. The partially insulated tip (or helix) 802 comprises one fully insulated section 804 and one uninsulated section 806. The partially insulated mesh 808 comprises a first area 810 of the mesh 808 which is insulated and second are 812 of the mesh 808 which is not insulated. The impedance of the catheter tip can be readily controlled by the amount of surface area of the helical tip itself and the area of the mesh (if present) which is insulated. With a fixed conductivity in the tip and the mesh (if present), the impedance can be increased by increasing the percentage of the surface area of the tip or mesh which is insulated.

A hole 820 is shown in the mesh 808. The mesh 808 may be flat and flush with the end 822 of the catheter 816 or may be partially wrapped (not shown) over the end 820 or inside the end 820 to affix the mesh to the catheter 816. The mesh 808 may also be hemispherical, truncated conical, truncated pyramidal or any other shape which may assist in allowing the mesh 808 to more compliantly contact tissue (not shown) surface to transmit the pacing signal or discharge. Within the catheter 816 may be a soluble, elutable or dispersible material which carries medication or biologically active material along with the catheter. For example, antiinflammatants, antibiotics, analgesics, pain-reducing medication, vitamins, anti-viral medication, or the like may be transmitted to the attachment site along with the catheter by inclusion within a material 814 carried within the catheter 816. The inner diameter or inner wall 817 of the catheter 816 is shown to encompass the entire volume of the drug delivery material 814.

The coating of insulation on the helical tip or mesh may be applied by any convenient method, including, but not limited to coating (e.g., dip coating), printing, spraying, brush application, resist application and removal and the like. The insulation may also contain active ingredients (such as those recited within material 814) to benefit the patient. The insulation carrying the active material must not be soluble, so a polymer or other material that is porous or has elutable materials must be used. The material delivery does not have to be coextensive with the life of the implant or the tip, and delivery of the material may be desirable only over a short time period after insertion of the helical tip and catheter.

A soluble or dispersible protective cap may also be placed over the helical tip to reduce the possibility of any incidental damage while catheterizing or moving the tip within a patient. As previously noted, the cap material should preferably be biocompatible or even digestible and may include such materials as natural and synthetic materials such as sugars, starches, gelation (unhardened), gums, resins, polymers, and the like. All components of the catheter and tip which are exposed to the tissue or fluids within a patient should be non-thrombogenic, and bio-acceptable. There are extensive classes of commercially available materials which meet these needs for metal, polymeric, composite and other materials described within the practice of the present invention.

It is to be understood that the above description is intended to be illustrative, and not restrictive. Although the use of the lead has been described for use in a cardiac pacing system, the lead could as well be applied to other types of body stimulating systems. Many other embodiments will be apparent to those of skill in the art upon reviewing the above description. The scope of the invention should, therefore, be determined with reference to the appended claims, along with the full scope of equivalents to which such claims are entitled.

What is claimed:

1. An implantable electrode with a helical tip comprising:
an electrode having a distal end and a proximal end; and
a helix disposed on said electrode, which helix is aligned along a radial axis of the electrode at said distal end; and
said helix having a coating of insulating material on it surface which covers from 5–95% of surface area of said helix beyond the distal end of the electrode, and a drug delivery system comprising an effective amount of a therapeutic drug, wherein at least the majority of the drug delivery system is within a location selected from the group consisting of I) within structural walls of the lead, ii) within a volume having at least 50% of its volume generally within an electrode axially projected area of the tip.

2. The implantable electrode of claim 1, wherein said helix has a coating of insulating material on it surface which covers from 10–90% of surface area of said helix beyond the distal end of the electrode.

3. The implantable electrode of claim 1, wherein said helix is electrically active.

4. The implantable electrode as recited in claim 1, wherein said helix is electrically inactive.

5. The implantable electrode of claim 1 wherein said drug delivery system comprises at least one therapeutically active ingredient dispersed or dissolved within an organic carrier material.

6. The implantable electrode of claim 1 wherein said drug delivery system comprises at least one therapeutically active ingredient carried within a molded element having a dimension of width which is less than or equal to the diameter of said helix.

7. An implantable electrode with a helical tip comprising:
an electrode having a distal end and a proximal end; and
a helix disposed on said electrode, which helix is aligned along a radial axis of the electrode at said distal end; and
said helix having a conductive porous surface at said distal end of said electrode said conductive porous surface at said distal end of said electrode comprising a mesh, wherein said mesh comprises an electrically conducting surface.

8. The implantable electrode of claim 7, wherein said mesh is electrically active.

9. The implantable electrode of claim 7, wherein said helix has at least part of its surface beyond said distal end of said electrode and said distal end of said electrode having a porous conductive surface, and at a base of said helix is said drug delivery system.

10. The implantable electrode of claim 7, wherein a conductive porous surface is at said distal end of said electrode and underneath said conductive porous surface, said drug delivery system is located.

11. The implantable electrode of claim 7 wherein said drug delivery system is selected from the group consisting of 1) a compacted tablet comprising more than 50% of the active ingredient, 2) an absorbent material which controllably releases the drug in contact with bodily fluids, 3) solid mass with dispersed, dissolved or emulsified therapeutically active ingredient which elutes, migrates, or dissolves from a carrier mass or continuous phase within the solid mass, and 4) encapsulated active ingredient which migrates through a porous or semipermeable shell or sheath.

12. A distal tip electrode adapted for implantation on or about the heart and for connection to a system for monitoring or stimulating cardiac activity, said electrode comprising:
an electrode tip;
a porous conductive element disposed at a distal end of the electrode tip;
a surface area at the distal end of the electrode tip,
a helix disposed within said electrode, said helix comprising a conductor disposed in a helical shape, wherein said helix travels along radial axis of the electrode through said surface area; and
a helix guiding mechanism for directing movement of the helix during travel, said distal tip electrode also having at least one feature comprising a drug delivery system for an effective amount of a therapeutic drug, wherein at least the majority of the drug delivery system is within a volume having at least 50% of its volume generally within an electrode axially projected area of the tip.

13. The distal tip electrode as recited in claim 12, wherein said helix is electrically active.

14. The distal tip electrode as recited in claim 12, wherein said helix is electrically inactive.

15. The distal tip electrode recited in claim 12 wherein the drug delivery system comprises a molded element of natural or synthetic resin having dispersed or dissolved therein a therapeutically active drug.

16. A distal tip electrode adapted for implantation on or about the heart and for connection to a system for monitoring or stimulating cardiac activity, said electrode comprising:
an electrode tip;
a porous conductive element disposed at a distal end of the electrode tip;
a surface area at the distal end of the electrode tip,
a helix disposed within said electrode, said helix comprising a conductor disposed in a helical shape, wherein said helix travels along radial axis of the electrode through said surface area; and
a helix guiding mechanism for directing movement of the helix during travel, said distal tip electrode also having at least one feature comprising a drug delivery system for an effective amount of a therapeutic drug, wherein at least the majority of the drug delivery system is within a location selected from the group consisting of I) within structural walls of the lead, ii) within a volume having at least 50% of its volume generally within an electrode axially projected area of the tip wherein said porous conductive element comprises a mesh screen.

17. The distal tip electrode as recited in claim 16, wherein said mesh screen is electrically active.

18. The distal tip electrode as recited in claim 16, wherein said helix is aligned with a radial axis of the electrode.

19. A distal tip electrode adapted for implantation on or about the heart and for connection to a system for monitoring or stimulating cardiac activity, said electrode comprising:
an electrode tip;
a porous conductive element disposed at a distal end of the electrode tip, said porous conductive element forming a surface;
a protuberance extending from said porous conductive element;
a helix disposed within said electrode, said helix comprises a conductor disposed in a helical shape, wherein said helix travels along radial axis of the electrode through said surface; and a helix guiding mechanism for directing movement of the helix during travel, said distal electrode tip further comprising in a drug delivery system of an effective amount of a therapeutic drug, wherein at least the majority of the drug delivery system is within a location selected from the group consisting of I) within structural walls of the lead, ii) within a volume having at least 50% of its volume generally within an electrode axially projected area of the tip.

20. The distal tip electrode as recited in claim 19, wherein said protuberance is disposed along said radial axis.

21. The distal tip electrode as recited in claim 19, wherein said helix guiding mechanism comprises a groove disposed within said porous conductive element.

22. The distal tip electrode as recited in claim 19, wherein said protuberance is positioned such that said helix coils around said protuberance during travel, and said protuberance comprises said drug delivery system.

23. The distal tip electrode as recited in claim 22, wherein said projection has a generally cylindrical cross-section.

24. A distal tip electrode adapted for implantation on or about the heart and for connection to a system for monitoring or stimulating cardiac activity, said electrode comprising:

an electrode tip;
a mesh screen disposed at a distal end of the electrode tip;
a surface at the distal end of the electrode tip,
a fixation device disposed within said electrode, said fixation device adapted for travel along radial axis of the electrode through said surface;
a guiding mechanism for directing movement of the fixation device during travel; and
a movement assembly, said movement assembly for providing movement to said fixation device, said distal tip electrode further comprising a drug delivery system comprising an effective amount of a therapeutic drug, wherein at least the majority of the drug delivery system is within a location selected from the group consisting of I) within structural walls of the lead, ii) within a volume having at least 50% of its volume generally within an electrode axially projected area of the tip.

25. The distal tip electrode as recited in claim 24, wherein said fixation device comprises a helix.

26. The distal tip electrode as recited in claim 24, wherein said movement assembly comprises a piston.

27. An electrode adapted for implantation on or about the heart and for connection to a system for monitoring or stimulating cardiac activity, said electrode comprising:

a lead body having a first end and a second end;
an electrode disposed proximate the first end of the lead body;
connector terminal disposed at said second end of the lead body, said connector terminal for connecting with a pulse generating unit;
an electrode tip disposed proximate one end of the electrode;
a surface at the distal end of the electrode tip, said surface further comprising an electrical conducting surface wherein said surface is comprised of a porous conductive element;
a helix disposed within said electrode, said helix comprising a conductor disposed in a helical shape, wherein said helix travels along radial axis of the electrode through said surface thereby placing said helix in extension and retraction;
a helix guiding groove for directing movement of the helix during extension and retraction of said helix, and said distal tip electrode further comprising a drug delivery system comprising an effective amount of a therapeutic drug, wherein at least the majority of the drug delivery system is within a location selected from the group consisting of I) within structural walls of the lead, ii) within a volume having at least 50% of its volume generally within an electrode axially projected area of the tip.

28. A system for delivering signals to the heart, said system comprising:

an electronics system including a cardiac activity sensor and a signal generator for producing signals to stimulate the heart; and
a lead adapted for implantation heart, said lead comprising:
an electrode tip;
a porous conductive element disposed at a distal end of the electrode tip;
a surface at the distal end of the electrode tip,
a helix disposed within said electrode, said helix comprises a conductor disposed in a helical shape, wherein said helix travels along radial axis of the electrode through said surface;
a helix guiding mechanism for directing movement of the helix during travel, and said distal tip electrode further comprising a drug delivery system comprising an effective amount of a therapeutic drug, wherein at least the majority of the drug delivery system is within a location selected from the group consisting of I) within structural walls of the lead, ii) within a volume having at least 50% of its volume generally within an electrode axially projected area of the tip.

29. A tip electrode, comprising:

a fixation helix having a surface with an electrically insulating coating thereon which electrically insulating coating covers less than all of the surface of said fixation helix, and within said helix is a drug delivery system comprising an effective amount of a therapeutic drug, wherein at least the majority of the drug delivery system is within a location selected from the group consisting of i) within structural walls of the lead, ii) within a volume having at least 50% of its volume generally within an electrode axially projected area of the tip.

30. An implantable electrode with a helical tip comprising:

an electrode having a distal end and a proximal end; and
a helix disposed on said electrode, which helix is aligned along a radial axis of the electrode at said distal end;
a housing for said helix; and
said implantable electrode having at least one feature selected from the group consisting of:
a) said helix having a coating of an insulating material on 5–95% of its surface,
b) said helix having at least part of its surface beyond said distal end of said electrode and said distal end of said electrode having a porous conductive surface,
c) a conductive porous surface at said distal end of said electrode, and
d) a porous conductive surface at the distal end of the electrode having an insulating coating covering from 5–95% of the surface of said porous conductive surface, and wherein at least 25% of the drug delivery system is provided in structural material for components of the implantable electrode selected from the group consisting of the housing, a piston, and a stylet.

31. An implantable electrode with a helical tip comprising:

an electrode having a distal end and a proximal end; and a helix disposed on said electrode, which helix is aligned along a radial axis of the electrode at said distal end;

a housing for said helix; and said implantable electrode having a feature selected from the group consisting of a) a coating of an insulating material on 5–95% of its surface, and b) a porous conductive surface at the distal end of the electrode having an insulating coating covering from 5–95% of the surface of said porous conductive surface, and wherein at least 25% of the drug delivery system is provided in structural material for components of the implantable electrode selected from the group consisting of the piston, and a stylet.

* * * * *